(12) United States Patent
Kendall et al.

(10) Patent No.: US 8,969,498 B2
(45) Date of Patent: Mar. 3, 2015

(54) COMPOSITIONS AND METHOD OF INHIBITING POLYMERIZATION OF VINYL-ARYL MONOMERS

(75) Inventors: Nathan T. Kendall, Midland, MI (US); Kishore K. Kar, Midland, MI (US); Mark H. McAdon, Midland, MI (US); Krzysztof Matyjaszewski, Pittsburgh, PA (US); Laura Mueller, Pittsburgh, PA (US); Charles D. Dukes, Midland, MI (US)

(73) Assignees: Dow Global Technologies LLC, Midland, MI (US); Carnegie Mellon University, Pittsburgh, PA (US)

( * ) Notice: Subject to any disclaimer, the term of this patent is extended or adjusted under 35 U.S.C. 154(b) by 146 days.

(21) Appl. No.: 13/811,574

(22) PCT Filed: Jul. 27, 2011

(86) PCT No.: PCT/US2011/045469
§ 371 (c)(1),
(2), (4) Date: Jan. 22, 2013

(87) PCT Pub. No.: WO2012/018650
PCT Pub. Date: Feb. 9, 2012

(65) Prior Publication Data
US 2013/0158203 A1 Jun. 20, 2013

Related U.S. Application Data

(60) Provisional application No. 61/369,854, filed on Aug. 2, 2010.

(51) Int. Cl.
| C07C 7/20 | (2006.01) |
| C08F 2/40 | (2006.01) |
| C08F 2/00 | (2006.01) |
| C08F 12/08 | (2006.01) |
| C08F 12/36 | (2006.01) |

(52) U.S. Cl.
CPC ... C07C 7/20 (2013.01); C08F 2/00 (2013.01); C08F 12/08 (2013.01); C08F 12/36 (2013.01)
USPC ......... 526/217; 525/256; 526/204; 526/220; 526/236; 526/346

(58) Field of Classification Search
CPC ............... C07C 7/20; C08F 2/00; C08F 2/40; C08F 12/00; C08F 12/08; C08F 12/36
USPC .......... 525/256, 259; 526/204, 217, 220, 236, 526/346; 564/225, 229, 230, 248, 270; 540/470, 473; 568/300
See application file for complete search history.

(56) References Cited

U.S. PATENT DOCUMENTS

| 3,520,943 A | 7/1970 | Albert |
| 3,524,894 A | 8/1970 | Albert |
| 5,854,234 A * | 12/1998 | Hansen et al. ............ 514/211.01 |
| 2003/0124378 A1 * | 7/2003 | Konarski et al. ............... 428/620 |
| 2009/0286978 A1 | 11/2009 | Minch et al. |

FOREIGN PATENT DOCUMENTS

| DE | 102005023607 | 11/2006 |
| EP | 0467850 | 1/1992 |
| EP | 1837322 | 9/2007 |
| WO | 0210100 | 2/2002 |

OTHER PUBLICATIONS

Machine translation of DE102005023607.*
Fu, X. et al. Chemical Communications vol. 47 pp. 8210-8222 published online May 4, 2011.*
Cotton, F. A. et al. Dalton Transactions vol. 35 pp. 3943-3951 published online Jul. 25, 2007.*
Moore, W.M. et al. Journal of Medicinal Chemistry vol. 39 pp. 669-672 published Feb. 2, 1996.*
Löfås, S. et al. Journal of the American Chemical Society vol. 107 pp. 7534-7541 published Dec. 1985.*
Protective Groups in Organic Synthesis, 3rd ed, Greene T.W. and Wuts P.G. Wiley-Interscience New York, 1999.

* cited by examiner

*Primary Examiner* — Irina S Zemel
*Assistant Examiner* — Jeffrey Lenihan
(74) *Attorney, Agent, or Firm* — Edward W. Black (57) ABSTRACT

The invention generally relates to a method of inhibiting polymerization of vinyl¬aryl monomers, a process for increasing number average molecular weight of a polystyrene, and to an inhibitor composition useful therein.

20 Claims, 1 Drawing Sheet

COMPOSITIONS AND METHOD OF INHIBITING POLYMERIZATION OF VINYL-ARYL MONOMERS

CROSS REFERENCE TO RELATED APPLICATION(S)

This application claims benefit of priority from U.S. Provisional Patent Application No. 61/369,854, filed Aug. 2, 2010, which application is incorporated by reference herein in its entirety.

BACKGROUND OF THE INVENTION

1. Field of the Invention

The invention generally relates to a method of inhibiting polymerization of vinyl-aryl monomers, a process for increasing number average molecular weight of a polystyrene, and to an inhibitor composition useful therein.

2. Background Art

Vinyl-aryl monomers can be polymerized to prepare aryl-containing polymers, which contain repeat units comprising residuals of the vinyl-aryl monomers. Examples of the vinyl-aryl monomers are styrene and divinylbenzenes. Examples of the aryl-containing polymers that can be prepared therefrom are polystyrene, poly(acrylonitrile-butadiene-styrene), poly(styrene-butadiene) rubber, poly(styrene-butadiene) latex, poly(styrene-isoprene-styrene), poly(styrene-divinylbenzene), polydivinylbenzene, and poly(styrene-divinylbenzene)-containing polyesters.

These and other aryl-containing polymers have found a wide variety of commercial uses. Examples of such commercial uses are building insulation, synthetic rubber, thermoplastics, fiberglass, piping, automobile and boat parts, food containers, carpet backing, and ion exchange resins.

Oftentimes, however, the vinyl-aryl monomers prematurely polymerize before they can be properly used to prepare the aryl-containing polymers. This premature or unwanted polymerization can occur throughout the lifetimes of the vinyl-aryl monomers starting from a time just after their synthesis and continuing through their subsequent purification, storage, and transportation. The unwanted polymerization prematurely consumes the vinyl-aryl monomers and leads to polymer and gel formation and fouling of equipment such as distillation columns.

The fouling of equipment has been a major problem in the chemicals and polymer industries. This is because manufacturing downtime caused by the fouling of equipment increases waste and manufacturing costs and can decrease product quality.

The chemicals and polymer industries have tried using inhibitors of polymerization of vinyl-aryl monomers to prevent such fouling, but with limited success. One commonly used inhibitor appears to be 2-(secondary-butyl)-4,6-dinitrophenol (DNBP), also known as 4,6-dinitro-2-(1-methylpropyl)-phenol and Dinoseb (CAS no. 88-85-7). The DNBP is used in liquid phases, but is toxic to humans and animals.

The premature polymerization of styrene in particular has also meant that it has been difficult to prepare high molecular weight polystyrene by a radical polymerization process. Ideally polymerization of styrene would be initiated by generating few styrene radicals, and then the few styrene radicals would propagate by consuming remaining styrene monomer to form a small number polystyrene chains until a high molecular weight polystyrene is formed. Unfortunately heating styrene monomer causes too many styrene radicals to spontaneously form. It is believed that these many styrene-derived radicals lead to a substantial increase in numbers of polystyrene chains, thereby undesirably leading to low molecular weight polystyrene.

There is a need in the chemicals and polymer industries for an improved method of inhibiting unwanted polymerization of the vinyl-aryl monomers until such time that polymerization thereof is desired, and for improved inhibitor compositions useful therein. There is also a need in the polymer industry for a process for preparing high molecular weight polystyrene via a radical polymerization process.

BRIEF SUMMARY OF THE INVENTION

The invention generally relates to an improved method of inhibiting polymerization of vinyl-aryl monomers until such time that polymerization thereof is desired, and to an inhibitor composition useful therein. The invention also generally relates to a process for preparing high molecular weight polystyrene via a radical polymerization process.

In a first embodiment the present invention provides an inhibitor composition comprising a mixture of a vinyl-aryl monomer and a polymerization-inhibiting effective amount of a substituted amidine of formula (I):

(I)

or a prototropic tautomer thereof,

Wherein: Z is 1,3-($C_3$ or $C_7$)hydrocarbylene or 1,3-($C_2$-$C_6$) heterohydrocarbylene such that ring (r) is a six-membered ring; benzo-fused six-membered ring wherein Z comprises a 3-atom linker portion having 2 contiguous ring carbon atoms that are fused to the benzo; or 5-membered or 6-membered heteroarylene-fused six-membered ring wherein Z comprises a 3-atom linker portion having 2 contiguous ring carbon atoms that are fused to the 5-membered or 6-membered heteroarylene, wherein when Z is unsubstituted, ring (r) is non-aromatic and when Z is substituted, ring (r) is non-aromatic or aromatic; and (a), (b), or (c): (a) X is $NR^{2a}$, $C(H)R^{2b}$, or O; and Each of $R^1$, $R^{2a}$, and $R^{2b}$ independently is a hydrogen atom, ($C_1$-$C_{20}$)hydrocarbyl, or $C_1$-$C_{20}$)heterohydrocarbyl; (b) X is $NR^{2a}$; and $R^1$ and $R^{2a}$ are taken together to form $Z^A$, wherein $Z^A$ independently is as defined for Z; or (c) X is C(H)$R^{2b}$; and $R^1$ and $R^{2b}$ independently are taken together to form $Z^A$, wherein $Z^A$ independently is as defined for Z; Wherein each heterohydrocarbylene, and heterohydrocarbyl independently comprises carbon atoms, hydrogen atoms, and 1 or 2 heteroatoms wherein each heteroatom independently is O, S, S(O), S(O)$_2$, or N($R^N$); Wherein each $R^N$ independently is a hydrogen atom or unsubstituted ($C_1$-$C_{20}$)alkyl; Wherein each benzo, heteroarylene, hydrocarbylene, heterohydrocarbylene, hydrocarbyl, and heterohydrocarbyl independently is unsubstituted or substituted with from 1 to 3 substituents $R^S$; and Wherein each $R^S$ independently is bonded to a carbon atom and is unsubstituted ($C_1$-$C_{10}$)alkyl, unsubstituted ($C_3$-$C_{10}$) cycloalkyl, unsubstituted ($C_1$-$C_{10}$)alkyl-O—, —OH, oxo (i.e., =O), or fluorine atom.

In another embodiment the present invention provides a method of inhibiting polymerization of a vinyl-aryl monomer, the method comprising contacting a vinyl-aryl monomer in need of polymerization inhibition treatment with a polymerization-inhibiting effective amount of the substituted amidine of formula (I) as described in the first embodiment, or the prototropic tautomer thereof, wherein the contacting is performed in such a way that polymerization of the vinyl-aryl monomer is inhibited.

In still another embodiment the present invention provides a process for building molecular weight of a polystyrene, the process comprising contacting a first polystyrene with a nitroxide radical source and a polymerization-inhibiting effective amount of the substituted amidine of formula (I) as described in the first embodiment, or the prototropic tautomer thereof, wherein the contacting is performed in such a way that the styrene monomer reacts with the first polystyrene so as to form a second polystyrene such that number average molecular weight of the second polystyrene is greater than number average molecular weight of the first polystyrene.

The substituted amidine of formula (I) as described in the first embodiment, and the prototropic tautomer thereof, are effective inhibitors of polymerization of vinyl-aryl monomers, including under conditions (e.g., distillation) wherein the vinyl-aryl monomers are susceptible to polymerization. Thus, the substituted amidine of formula (I) and prototropic tautomer thereof and the invention inhibitor composition are useful in the invention method. In the invention method, the invention inhibitor composition is useful for inhibiting polymerization of the vinyl-aryl monomer until such a time that polymerization of the vinyl-aryl monomer is desired. Further, the substituted amidine of formula (I) and invention inhibitor composition are useful in the invention process for increasing number average molecular weight of a polystyrene.

Thus, the invention is valuable to the chemical and polymer industries, especially where inhibiting unwanted polymerization of the vinyl-aryl monomers is desired. Examples of ways such industries could employ the invention are in production, purification, storage, and transportation of vinyl-aryl monomers and in production of higher number average molecular weight polystyrene.

The term "prototropic tautomer" means an isomer that can readily interconvert with another isomer by exchanging a proton as illustrated for formula (I) by the following equilibrium: —N=C—N(H)— ⇌ —(H)N—C=N—).

The phrase "polymerization-inhibiting effective amount" means a quantity of a substance that is sufficient to delay onset of, reduce degree of, or, preferably prevent polymerization. More preferred is any combination thereof. The phrase "reduce degree of" typically means lessen a quantity of any oligomer or polymer (e.g., gel) produced by one of such reactions compared to a quantity of oligomer or polymer produced by a reaction lacking the substance. The polymerization-inhibiting effective amount can be expressed as an absolute weight (e.g., in grams) or relative weight (e.g., expressed in parts per million (ppm) or weight percent (wt %)). For example, 1 ppm equals 1 milligram per 1000 grams (or 1 gram per 1000 kilograms, and the like) or 0.0001 wt %.

The term "vinyl-aryl monomer" means a $(C_6-C_{18})$aryl bonded to at least one functional group of formula —C(H)=CH$_2$. The term "$(C_6-C_{18})$aryl" and other chemical terms are defined later.

Additional embodiments are described in accompanying drawing(s) and the remainder of the specification, including the claims.

BRIEF DESCRIPTION OF THE DRAWING(S)

Some embodiments of the present invention are described herein in relation to the accompanying drawing(s), which will at least assist in illustrating various features of the embodiments.

DETAILED DESCRIPTION OF THE INVENTION

The invention relates to the method of inhibiting polymerization of vinyl-aryl monomers, process for increasing number average molecular weight of a polystyrene, and to the inhibitor composition useful therein, as summarized previously.

For purposes of United States patent practice and other patent practices allowing incorporation of subject matter by reference, the entire contents—unless otherwise indicated—of each U.S. patent, U.S. patent application, U.S. patent application publication, PCT international patent application and WO publication equivalent thereof, referenced in the instant Summary or Detailed Description of the Invention are hereby incorporated by reference. In an event where there is a conflict between what is written in the present specification and what is written in a patent, patent application, or patent application publication, or a portion thereof that is incorporated by reference, what is written in the present specification controls.

In the present application, any lower limit of a range of numbers, or any preferred lower limit of the range, may be combined with any upper limit of the range, or any preferred upper limit of the range, to define a preferred aspect or embodiment of the range. Unless otherwise indicated, each range of numbers includes all numbers, both rational and irrational numbers, subsumed within that range (e.g., the range from about 1 to about 5 includes, for example, 1, 1.5, 2, 2.75, 3, 3.80, 4, and 5).

The word "optionally" means "with or without." For example, "optionally, an additive" means with or without an additive.

In an event where there is a conflict between a compound name and its structure, the structure controls.

In an event where there is a conflict between a unit value that is recited without parentheses, e.g., 2 inches, and a corresponding unit value that is parenthetically recited, e.g., (5 centimeters), the unit value recited without parentheses controls.

As used herein, "a," "an," "the," "at least one," and "one or more" are used interchangeably. In any aspect or embodiment of the instant invention described herein, the term "about" in a phrase referring to a numerical value may be deleted from the phrase to give another aspect or embodiment of the instant invention. In the former aspects or embodiments employing the term "about," meaning of "about" can be construed from context of its use. Preferably "about" means from 90 percent to 100 percent of the numerical value, from 100 percent to 110 percent of the numerical value, or from 90 percent to 110 percent of the numerical value. In any aspect or embodiment of the instant invention described herein, the open-ended terms "comprising," "comprises," and the like (which are synonymous with "including," "having," and "characterized by") may be replaced by the respective partially closed phrases "consisting essentially of," "consists essentially of," and the like or the respective closed phrases "consisting of," "consists of," and the like to give another aspect or embodiment of the instant invention. The partially closed phrases such as "consisting essentially of" and the like limits scope of a claim to materials or steps recited therein and those that do not materially affect the basic and novel characteristic(s) of the claimed invention. The term "characterizable" is open-ended and means distinguishable.

In the present application, when referring to a preceding list of elements (e.g., ingredients), the phrases "mixture thereof," "combination thereof," and the like mean any two or more, including all, of the listed elements. The term "or" used in a listing of members, unless stated otherwise, refers to the listed members individually as well as in any combination, and supports additional embodiments reciting any one of the individual members (e.g., in an embodiment reciting the phrase "10 percent or more," the "or" supports another embodiment reciting "10 percent" and still another embodiment reciting "more than 10 percent."). The term "plurality" means two or more, wherein each plurality is independently selected unless indicated otherwise. The term "independently" means separately without regard for another. The terms "first," "second," et cetera serve as a convenient means of distinguishing between two or more elements or limitations (e.g., a first chair and a second chair) and do not imply quantity or order unless specifically so indicated. The symbols "≤" and "≥" respectively mean less than or equal to and greater than or equal to. The symbols "<" and ">" respectively mean less than and greater than. The term "characterizable" means capable of being distinguished, if desired.

Any headings herein are used only for convenience of the reader and do not limit, and should not be interpreted as limiting, the present invention.

Where the invention, or a portion or preferred embodiment thereof, is defined in the alternative by one or more Markush groups, wherein each Markush group independently consists of its own members (e.g., for illustration purposes a general Markush group "A" consisting of members A1, A2, and A3; or Markush group "A3" consisting of preferred members A3a, A3b, A3c, and A3d), the invention contemplates preferred embodiments that (i) select any single member from one of the one or more Markush groups (e.g., for illustration purposes selecting A2 from Markush group A or selecting A3c from Markush group A3), thereby limiting scope of the one Markush group (e.g., A or A3) to the selected single member (e.g., A2 or A3c); or (ii) delete any single member from one of the one or more Markush groups (e.g., for illustration purposes deleting A1 from Markush group A or deleting A3a from Markush group A3), thereby limiting the one Markush group (e.g., A or A3) to the remaining members thereof (e.g., to A2 and A3 remaining in Markush group A or to A3b, A3c, and A3d remaining in Markush group A3). In some embodiments the member that is selected or deleted is chosen from any one of the members of the one Markush group that is illustrated in one of the Examples or other species of the present invention described herein.

This specification may refer to certain well-known testing standards promulgated by certain organizations, which are referred to herein by their acronyms. The acronym "ANSI" stands for American National Standards Institute, the name of an organization headquartered in Washington, D.C., USA. The acronym "ASTM" stands for ASTM International, the name of an organization headquartered in West Conshohocken, Pa., USA; ASTM International was previously known as the American Society for Testing and Materials. The acronym "DIN" stands for Deutsches Institut für Normung e. V., the name of an organization headquartered in Berlin, Germany. The acronym "ISO" stands for International Organization for Standardization, the name of an organization headquartered in Geneva 20, Switzerland.

Unless otherwise noted, the phrase "Periodic Table of the Elements" refers to the official periodic table, version dated Jun. 22, 2007, published by the International Union of Pure and Applied Chemistry (IUPAC). Also any references to a Group or Groups shall be to the Group or Groups reflected in this Periodic Table of the Elements.

Certain unsubstituted chemical groups are described herein as having a maximum number of 40 carbon atoms (e.g., $(C_1-C_{40})$hydrocarbyl and $(C_1-C_{40})$heterohydrocarbyl) for substituent groups (e.g., R groups) where number of carbon atoms is not critical. Forty carbon atoms, more preferably 20 carbon atoms, and still more preferably 10 carbon atoms in such unsubstituted chemical groups is a practical upper limit; nevertheless in some embodiments the invention contemplates such unsubstituted groups having a maximum number of carbon atoms that is higher than 40 (e.g., 100, 1000, or more).

The term "hydrocarbyl" means an alkyl, cycloalkyl, or aryl radical of at least 1, 3, or 6 carbon atoms, respectively, or a combination thereof (e.g., aryl-alkyl and alkyl-aryl). Preferred alkyl, cycloalkyl, and aryl is $(C_1-C_{10})$alkyl, $(C_3-C_{10})$cycloalkyl, and $(C_6-C_{18})$aryl respectively. The term "hydrocarbylene" means a diradical version of hydrocarbyl, i.e., an alkylene, cycloalkylene, or arylene, respectively, or a combination thereof (e.g., arylene-alkyl). The term "1,3-" as in "1,3-hydrocarbylene" means the diradical version of hydrocarbyl is a 1,3-diradical wherein at least one of the radicals is on a non-aromatic carbon atom. The term "heterohydrocarbyl" means a heteroalkyl, heterocycloalkyl, or heteroaryl of at least 1, 2, or 1 carbon atoms, respectively. Preferred heteroalkyl, heterocycloalkyl, and heteroaryl is $(C_1-C_{10})$heteroalkyl, $(C_2-C_{10})$heterocyclo alkyl, and $(C_1-C_4)$heteroaryl respectively. The term "heterohydrocarbylene" means a diradical version of heterohydrocarbyl, i.e., a heteroalkylene, heterocycloalkylene, or heteroarylene, or a combination thereof (e.g., heteroarylene-alkyl). The term "1,3-" as in "1,3-heterohydrocarbylene" means the diradical version of heterohydrocarbyl is a 1,3-diradical wherein at least one of the radicals is on a non-aromatic atom.

The terms "$(C_1-C_{10})$alkyl" means a saturated straight or branched hydrocarbon radical of from 1 to 10 carbon atoms. The hydrocarbon radical is unsubstituted or substituted by one or more $R^S$. Other alkyl groups (e.g., $(C_1-C_6)$alkyl)) are defined in an analogous manner. Preferably, $(C_1-C_{10})$alkyl has a maximum of 8 carbon atoms (i.e., $(C_1-C_8)$alkyl), more preferably 6 carbon atoms, and still more preferably 5 carbon atoms. Examples of unsubstituted $(C_1-C_{10})$alkyl are unsubstituted $(C_1-C_6)$alkyl; unsubstituted $(C_1-C_5)$alkyl; methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted $(C_1-C_{10})$alkyl are substituted $(C_1-C_6)$alkyl and $(C_{15})$alkyl. The $(C_{15})$alkyl is, for example, a $(C_{10})$alkyl substituted by one $R^S$ that is a $(C_5)$ alkyl. Preferably, each $(C_1-C_{10})$alkyl is methyl.

The term "$(C_2-C_4)$alkylene" means a saturated straight chain or branched chain diradical (i.e., the radicals are not on ring atoms and not on a same carbon atom) of from 2 to 4 carbon atoms. The chain diradical is unsubstituted or substituted by one or more $R^S$. Other alkylene groups (e.g., $(C_3)$alkylene)) are defined in an analogous manner. Examples of unsubstituted $(C_2-C_4)$alkylene are unsubstituted 1,3-$(C_3)$alkylene; unsubstituted 1,2-$(C_2-C_4)$alkylene; 1,3-$(C_3-C_4)$alkylene; 1,4-$(C_4)$alkylene; —CH$_2$CH$_2$—, —(CH$_2$)$_3$—, —CH$_2$CHCH$_3$, and —(CH$_2$)$_4$—. Examples of substituted $(C_2-C_4)$alkylene are substituted $(C_2-C_3)$alkylene, —CF$_2$CH$_2$CH$_2$—, and —CH$_2$C(CH$_3$)$_2$CH$_2$—. Preferably $(C_2-C_4)$alkylene is —CH$_2$CH$_2$CH$_2$—.

The terms "$(C_3-C_{10})$cycloalkyl" mean a saturated or unsaturated (but not aromatic) cyclic hydrocarbon radical of from 3 to 10 carbon atoms. The cyclic hydrocarbon radical is unsubstituted or substituted by one or more $R^S$. Other cycloalkyl groups (e.g., $(C_3-C_6)$alkyl)) are defined in an analogous manner. When $(C_3-C_{10})$cycloalkyl is unsaturated it is mono-unsaturated (i.e., contains 1 carbon-carbon double bond). Preferably $(C_3-C_{10})$cycloalkyl is saturated. Preferably, $(C_3-C_{10})$cycloalkyl has a maximum of 8 carbon atoms (i.e., $(C_3-C_8)$cycloalkyl), more preferably 6 carbon atoms, and still more preferably 5 carbon atoms. Examples of unsubstituted $(C_3-C_{10})$cycloalkyl are unsubstituted $(C_3-C_{80})$cycloalkyl, cyclopropyl, cyclobutyl, cyclopentyl, cyclohexyl, cycloheptyl, cyclooctyl, cyclononyl, and cyclodecyl. Examples of substituted $(C_3-C_{10})$cycloalkyl are substituted $(C_3-C_8)$cycloalkyl, 2-methylcyclopentyl, and 1-fluorocyclohexyl.

The term "$(C_1-C_{10})$heteroalkyl" means a saturated straight or branched heterohydrocarbon radical of from 1 to 10 carbon and 1 or 2 heteroatoms. The heterohydrocarbon radical is unsubstituted or substituted by one or more $R^S$. Other heteroalkyl groups (e.g., $(C_1-C_6)$heteroalkyl)) are defined in an analogous manner. Examples of unsubstituted $(C_1-C_{10})$heteroalkyl are unsubstituted $(C_1-C_8)$heteroalkyl; unsubstituted $(C_1-C_5)$heteroalkyl; methoxy; ethylamino; and diethylamino. Examples of substituted $(C_1-C_{10})$heteroalkyl are substituted $(C_1-C_8)$heteroalkyl and $(C_{15})$heteroalkyl. The $(C_{15})$heteroalkyl is, for example, a $(C_{10})$heteroalkyl substituted by one $R^S$, which is a $(C_5)$alkyl. Preferably, each $(C_1-C_{10})$heteroalkyl is methoxy.

The term "$(C_1-C_3)$heteroalkylene" means a saturated straight chain or branched chain diradical (i.e., the radicals are not on ring atoms) of from 1 to 3 carbon atoms and 1 heteroatom. The chain diradical is unsubstituted or substituted by one or more $R^S$. Other heteroalkylene groups (e.g., $(C_2)$alkylene)) are defined in an analogous manner. Examples of unsubstituted $(C_1-C_3)$heteroalkylene are —O—CH$_2$CH$_2$CH$_2$—, —CH$_2$CH$_2$—N(H)CH$_2$—, —CH$_2$—S—CH$_2$—, and —S(O)$_2$(CH$_2$)$_4$—. Examples of substituted $(C_1-C_3)$heteroalkylene are substituted $(C_2)$heteroalkylene, —O—CF$_2$CH$_2$CH$_2$—, and —CH$_2$—S—CH$_2$C(CH$_3$)$_2$CH$_2$—.

The term "$(C_2-C_{10})$heterocycloalkyl" means a saturated or unsaturated (but not aromatic) cyclic heterohydrocarbon radical of from 2 to 10 carbon atoms and 1 or 2 heteroatoms. The cyclic heterohydrocarbon radical is unsubstituted or substituted by one or more $R^S$. Other heterocycloalkyl groups (e.g., $(C_2-C_5)$heterocycloalkyl)) are defined in an analogous manner. When $(C_2-C_{10})$heterocycloalkyl is unsaturated, it is mono-unsaturated (i.e., contains 1 carbon-carbon or carbon-nitrogen double bond). Preferably $(C_2-C_{10})$heterocycloalkyl is saturated. Preferably, $(C_2-C_{10})$heterocycloalkyl has a maximum of 6 carbon atoms (i.e., $(C_2-C_6)$heterocycloalkyl), more preferably 5 carbon atoms, and still more preferably 4 carbon atoms. Examples of $(C_2-C_{10})$heterocycloalkyl are unsubstituted $(C_2-C_6)$heterocycloalkyl, aziridin-1-yl, oxetan-2-yl, tetrahydrofuran-3-yl, pyrrolidin-1-yl, tetrahydrothiophen-S,S-dioxide-2-yl, morpholin-4-yl, 1,4-dioxan-2-yl, hexahydroazepin-4-yl, 3-oxa-cyclooctyl, 5-thia-cyclononyl, and 2-aza-cyclodecyl.

The term "5-membered heteroarylene" means a cyclic aromatic heterohydrocarbon 1,2-diradical of 3 or 4 carbon atoms and 2 or 1 heteroatoms O, S, or N($R^N$), respectively. The term "6-membered heteroarylene" means a cyclic aromatic heterohydrocarbon 1,2-diradical of 4 or 5 carbon atoms and 2 or 1 nitrogen (N) atoms, respectively.

Unless otherwise noted the term "heteroatom" means O, S, S(O), S(O)$_2$, or N($R^N$), wherein independently each $R^N$ is a hydrogen atom, unsubstituted $(C_1-C_{20})$alkyl or $(C_3-C_{20})$cycloalkyl. Preferably each $R^N$ is a hydrogen atom or methyl.

As mentioned before, in some embodiments the invention employs a vinyl-aryl monomer. The term "vinyl-aryl monomer" means a polymerizable molecule comprising a $(C_6-C_{18})$ aryl covalently bonded to at least one functional group of formula —C(H)=CH$_2$. The vinyl-aryl can be interchangeably referred to as $(C_6-C_{18})$aryl-(C(H)=CH$_2$)$_q$, wherein q is an integer of from 1 to 3. When q is 1, the $(C_6-C_{18})$aryl-(C(H)=CH$_2$)$_q$ becomes $(C_6-C_{18})$aryl-C(H)=CH$_2$, when q is 2 the $(C_6-C_{18})$aryl-(C(H)=CH$_2$)$_q$ becomes H$_2$C=C(H)—$(C_6-C_{18})$arylene-C(H)=CH$_2$, and when q is 3 the $(C_6-C_{18})$aryl-(C(H)=CH$_2$)$_q$ becomes a H$_2$C=C(H)-[$(C_6-C_{18})$aromatic-triradical]-(C(H)=CH$_2$)$_2$.

The term "$(C_6-C_{18})$aryl" means a mono-, bi- or tricyclic aromatic hydrocarbon radical of from 6 to 18 carbon atoms, of which at least from 6 to 14 of the carbon atoms are aromatic ring carbon atoms, and the mono-, bi- or tricyclic radical comprises 1, 2 or 3 rings, respectively; wherein the 1 ring is aromatic and the 2 or 3 rings independently are fused or non-fused and at least one of the 2 or 3 rings is aromatic. The aromatic hydrocarbon radical is unsubstituted substituted by one or more $R^S$. In the $(C_6-C_{18})$aryl of the vinyl-aryl monomer, there can be 3$R^S$ when q is 3, 4$R^S$ when q is 2, and 5$R^S$ when q is 1. Preferably, there is 1, and more preferably 0$R^S$ in the $(C_6-C_{18})$aryl of the vinyl-aryl monomer. The terms "$(C_6-C_{18})$arylene" and "[$(C_6-C_{18})$aromatic-triradical]" respectively mean a diradical and triradical analog of $(C_6-C_{18})$aryl. Other aryl groups (e.g., $(C_6-C_{10})$aryl)) are defined in an analogous manner. Preferably, $(C_6-C_{18})$aryl has a maximum of 14 carbon atoms (i.e., $(C_6-C_{14})$aryl), more preferably 10 carbon atoms, still more preferably 9 carbon atoms, and even more preferably 6 carbon atoms. Examples of unsubstituted $(C_6-C_{18})$aryl-(C(H)=CH$_2$)$_q$ are styrene (q=1); 1,2-divinylbenzene, 1,3-divinylbenzene, 1,4-divinylbenzene, and a mixture of 1,3-divinylbenzene and 1,4-divinylbenzene (all divinylbenzenes q=2); 1-vinylnaphthalene (q=1); and 1,3,5-trivinylbenzene (q=3). Examples of $R^S$-substituted $(C_6-C_{18})$aryl-(C(H)=CH$_2$)$_q$ are 4-methylstyrene (q=1); 2-fluoro-1,3-divinylbenzene (q=2); and 4-cyclohexyl-1-vinylnaphthalene (q=1). Preferably the vinyl-aryl monomer is a divinylbenzene, styrene, or a mixture of any two or three thereof. In some embodiments vinyl-aryl monomer is styrene. In some embodiments vinyl-aryl monomer is a mixture of 1,3- and 1,4-divinylbenzenes. In some embodiments vinyl-aryl monomer is a mixture of styrene and at least one divinylbenzene.

In some embodiments of the substituted amidine of formula (I) and the prototropic tautomer thereof, X is NR$^{2a}$ or O. In other embodiments X is NR$^{2a}$ or C(H)R$^{2b}$. In still other embodiments X is C(H)R$^{2b}$ or O.

In some embodiments Z is the 1,3-$(C_3$ or $C_7)$hydrocarbylene, 1,3-$(C_3$ or $C_7)$hydrocarbylene is $(C_3)$alkylene, and X is —NR$^{2a}$R$^{2b}$ such that the substituted amidine of formula (I) is a compound of formula (II):

(II)

or a prototropic tautomer thereof, wherein m is an integer of from 0 to 3 and R$^1$ and R$^{2a}$ are as defined in (a) or (b) of the first embodiment. Preferably in formula (II), or the prototropic tautomer thereof, (b) R$^1$ and R$^{2a}$ are taken together to form a $(C_2-C_4)$alkylene or $(C_1-C_3)$heteroalkylene.

More preferably, R$^1$ and R$^{2a}$ are taken together to form Z$^A$, wherein Z$^A$ independently is as defined for Z. Still more preferably Z$^A$ is 1,3-$(C_3$ or $C_7)$hydrocarbylene; 1,3-$(C_3$ or $C_7$)hydrocarbylene of $Z^A$ is a 1,3-($C_3$)alkylene such that the compound of formula (II) is a compound of formula (IIa):

$$(R^S)_m \underset{\underset{H}{N}}{\overset{N}{\diagup}} (R^S)_n, \tag{IIa}$$

or a prototropic tautomer thereof, wherein (s) is a six-membered ring and n is an integer of form 0 to 3. Still more preferably each of m and n independently is 0 or 1. Even more preferably, m and n are each 0 such that the compound of formula (IIa) is compound (g1):

$$\tag{g1}$$

or the prototropic tautomer thereof. Compound (g1) is named 1,5,7-triazabicyclo[4.4.0]dec-5-ene, and is also known as 2,3,4,6,7,8-hexahydro-1H-pyrimido[1,2-a]pyrimidine. Compound (g1) has a pKa of 26.

Also even more preferably, each of m and n is 2 such that the compound of formula (IIa) is compound (g2), (g3), or (g7):

$$\tag{g2}$$

$$\tag{g3}$$

$$\tag{g7}$$

(g7), or the prototropic tautomer thereof. Compound (g2) is named 3,3,7,7-tetrafluoro-2,3,4,6,7,8-hexahydro-1H-pyrimido[1,2-a]pyrimidine. Compound (g3) is named 3,3,7,7-tetramethyl-2,3,4,6,7,8-hexahydro-1H-pyrimido[1,2-a]pyrimidine. Compound (g7) is named 6,8-dihydro-1H-pyrimido[1,2-a]pyrimidine-3,7(2H,4H)-dione.

In some embodiments of the compound of formula (II), or the prototropic tautomer thereof, (a) $R^1$ is a hydrogen atom, ($C_1$-$C_{20}$)alkyl, ($C_1$-$C_{20}$)heteroalkyl, ($C_3$-$C_{20}$)cycloalkyl, or ($C_2$-$C_{20}$)heterocycloalkyl; and $R^{2a}$ is a hydrogen atom, ($C_1$-$C_{20}$)alkyl, ($C_1$-$C_{20}$)heteroalkyl, ($C_3$-$C_{20}$)cycloalkyl, or ($C_2$-$C_{20}$)heterocycloalkyl. Preferably, $R^1$ is a hydrogen atom and $R^{2a}$ is ($C_1$-$C_6$)alkyl. More preferably, the compound of formula (II) is compound (g4):

$$\tag{g4}$$

or the prototropic tautomer thereof. Compound (g4) is named 1-methyl-1,4,5,6-tetrahydropyrimidin-2-amine.

Also preferably in the compound of formula (II), or the prototropic tautomer thereof, $R^1$ is ($C_1$-$C_6$)alkyl and $R^{2a}$ is a hydrogen atom. More preferably, the compound of formula (II) is compound (g5):

$$\tag{g5}$$

or the prototropic tautomer thereof. Compound (g5) is named N-(tetrahydropyrimidin-2(1H)-ylidene)methanamine.

In some embodiments of the compound of formula (II), or the prototropic tautomer thereof, $R^1$ is ($C_1$-$C_6$)alkyl and $R^{2a}$ is ($C_1$-$C_6$)alkyl. More preferably, the compound of formula (II) is compound (g6):

$$\tag{g6}$$

or the prototropic tautomer thereof. Compound (g6) is named N,1-dimethyl-1,4,5,6-tetrahydropyrimidin-2-amine.

In some embodiments X is O such that the substituted amidine of formula (I) is a compound of formula (III):

$$(R^S)_m \tag{III}$$

or a prototropic tautomer thereof, wherein m is an integer of from 0 to 3. More preferably, the compound of formula (III) is compound (i1) or (i2):

$$\tag{i1}$$

$$\tag{i2}$$

or the prototropic tautomer thereof. Compound (i1) is named (Z)—N-(1,3-oxazinan-2-ylidene)methanamine. Compound (i2) is named 5,6-dihydro-4H-1,3-oxazin-2-amine.

In some embodiments X is C(H)R$^{2b}$ such that the substituted amidine of formula (I) is a compound of formula (IV):

(IV)

or a prototropic tautomer thereof, wherein m is an integer of from 0 to 3 and R$^1$ and R$^{2b}$ are as defined in (a) or (c) of the first embodiment. Preferably, R$^1$ and R$^{2b}$ are taken together to form Z$^A$, wherein Z$^A$ independently is as defined for Z. More preferably Z$^A$ is 1,3-(C$_3$ or C$_7$)hydrocarbylene; 1,3-(C$_3$ or C$_7$)hydrocarbylene is a 1,3-(C$_3$)alkylene such that the compound of formula (IV) is a compound of formula (IVa):

(IVa)

or a prototropic tautomer thereof, wherein (s) is a six-membered ring and n is an integer of form 0 to 3. More preferably, the compound of formula (IVa) is any one of compounds (c1) to (c3):

(c1)

(c2) and

(c3)

or the prototropic tautomer thereof. Compound (c1) is named 1,2,3,4,4a,5,6,7-octahydro-1,8-naphthyridine. Compound (c2) is named 3,6-dimethyl-1,2,3,4,4a,5,6,7-octahydro-1,8-naphthyridine. Compound (c3) is named 3,6-difluoro-1,2,3,4,4a,5,6,7-octahydro-1,8-naphthyridine.

In some embodiments the compound of formula (IV) is compound (c4) or (c5):

(c4)

(c5)

or the prototropic tautomer thereof. Compound (c4) is named 3,4,5,6-tetrahydropyridin-2-amine. Compound (c5) is named (E)-N-(piperidin-2-ylidene)methanamine.

When m is 0, (R$^S$)$_m$ is absent and when n is 0, (R$^S$)$_n$ is absent.

When the substituted amidine of formula (I) contains rings (r) and (s) as in formula (IIa) or (IVa), preferably ring atoms in, and substituents on, one of rings (r) and (s) are the same as in and on the other. More preferably the only differences between rings (r) and (s) are due to stereochemistry, if any, or due to the amidine prototropic tautomers, and still more preferably only due to the amidine prototropic tautomers such that but for the prototropic tautomerism a vertical plane of symmetry would bisect X and the amidine carbon atom (i.e., =C<)) in formula (IIa) or (IVa).

As mentioned previously the invention employs the polymerization-inhibiting effective amount of the substituted amidine of formula (I). The invention contemplates employing any amount sufficient to achieve a desired degree of inhibition of polymerization of the vinyl-aryl monomer. From a material cost perspective, it can be desirable to employ a minimum inhibiting amount, or near the minimum inhibiting amount, of the substituted amidine of formula (I) necessary to achieve inhibition of polymerization of the vinyl-aryl monomer. In some embodiments, however, it may be desirable to employ substantially more than the minimum inhibiting amount, especially where economic factors like equipment downtime costs, process interruption costs, and the like can outweigh material costs. In some embodiments employing the substantially more amounts might also be desirable where polymerization inhibition effectiveness of the invention inhibitor composition might decrease over time (e.g., due to the substituted amidine of formula (I) being consumed in the invention method).

Without wishing to be bound by theory, in some embodiments the invention contemplates improved inhibition of polymerization of the vinyl-aryl monomer when the NH in the substituted amidine of formula (I), or the prototropic tautomer thereof, is characterizable by a pKa of from 25 to 27 compared to when pKa of the NH is less than 25. Accordingly in some embodiments the substituted amidine of formula (I), or the prototropic tautomer thereof, is characterizable by a pKa of from 25 to 27, and more preferably a pKa of 26±0.4. The term "pKa" means a negative logarithm (in base 10) of an acid dissociation constant K$_a$. The acid dissociation constant is also known as acidity constant and acid-ionization constant. As used herein, pKa of the substituted amidine of formula (I) refers to K$_a$ for the hydrogen atom shown in formula (I) (i.e., the hydrogen atom that is shown bonded to the right-most nitrogen atom in formula (I)).

In some embodiments the polymerization-inhibiting effective amount of the substituted amidine of formula (I) and the prototropic tautomer thereof is 40 parts per million (ppm) or higher of the substituted amidine of formula (I) relative to (based on) the vinyl-aryl monomer (i.e., greater than or equal to 40 parts of the substituted amidine of formula (I) per million parts of the vinyl-aryl monomer). In other embodiments such polymerization-inhibiting effective amount is 50 ppm or higher, in still other embodiments 500 ppm or higher, in still other embodiments 1000 ppm or higher, and even in other embodiments 5,000 ppm or higher. In other embodiments the polymerization-inhibiting effective amount of the substituted amidine of formula (I) and the prototropic tautomer thereof relative to the vinyl-aryl monomer is 20,000 ppm or lower, in still other embodiments 10,000 ppm or lower, in still other embodiments 5,000 ppm or lower, and even in other embodiments 100 ppm or lower.

In some embodiments the mixture of the inhibitor composition further comprises one or more vinyl-aryl monomer polymerization inhibitors other than the substituted amidine of formula (I) or prototropic tautomer thereof. The term "vinyl-aryl monomer polymerization inhibitor" means a molecule that is capable of delaying onset of the aforementioned reaction between one vinyl-aryl monomer molecule and another vinyl-aryl monomer molecule, diminishing the quantity of any oligomer or polymer (e.g., gel) produced by the reaction, increasing the period of time to produce a given quantity of the oligomer or polymer, or any combination thereof. Examples of the vinyl-aryl monomer polymerization inhibitor are the substituted amidine of formula (I), the prototropic tautomer thereof, and the one or more vinyl-aryl monomer polymerization inhibitors other than the substituted amidine of formula (I) or prototropic tautomer thereof. Preferred examples of the one or more vinyl-aryl monomer polymerization inhibitors other than the substituted amidine of formula (I) or prototropic tautomer thereof are 2,2,6,6-tetramethylpiperidine-1-oxyl (TEMPO), a 4-monosubstituted 2,2,6,6-tetramethylpiperidine-1-oxyl (i.e., a 4-monosubstituted TEMPO), and molecular oxygen (e.g., as air).

It can be desirable to employ the one or more additional vinyl-aryl monomer polymerization inhibitors other than the substituted amidine of formula (I) or prototropic tautomer thereof for economic reasons or technical reasons. For example, such additional vinyl-aryl monomer polymerization inhibitor(s) might be less expensive than the substituted amidine of formula (I) or prototropic tautomer thereof, and thus employing the less expensive former may allow use of less of the more expensive latter. Some of the one or more additional vinyl-aryl monomer polymerization inhibitors other than the substituted amidine of formula (I) or prototropic tautomer thereof can be promiscuous, that is can be capable of inhibiting polymerization of the vinyl-aryl monomers, vinyl monomers other than the vinyl-aryl monomers (e.g., acrylic monomers), or both. Thus, another example is an embodiment wherein the invention inhibitor composition further comprises the vinyl monomer other than vinyl-aryl monomers.

In some embodiments the one or more vinyl-aryl monomer polymerization inhibitors other than the substituted amidine of formula (I) or prototropic tautomer thereof comprises the aforementioned molecular oxygen, 2,2,6,6-tetramethylpiperidine-1-oxyl (TEMPO), the 4-monosubstituted 2,2,6,6-tetramethylpiperidine-1-oxyl, or a combination thereof. In some such embodiments, the one or more vinyl-aryl monomer polymerization inhibitors other than the substituted amidine of formula (I) or prototropic tautomer thereof is TEMPO. In some embodiments the one or more vinyl-aryl monomer polymerization inhibitors other than the substituted amidine of formula (I) or prototropic tautomer thereof comprises the 4-monosubstituted 2,2,6,6-tetramethylpiperidine-1-oxyl. Preferably, the 4-monosubstituted 2,2,6,6-tetramethylpiperidine-1-oxyl is 4-butoxy-2,2,6,6-tetramethylpiperidine-1-oxyl (4-butoxy-TEMPO), and more preferably 4-hydroxy-2,2,6,6-tetramethylpiperidine-1-oxyl (4-hydroxy-TEMPO) or 4-oxo-2,2,6,6-tetramethylpiperidine-1-oxyl (4-oxo-TEMPO). More preferably, the TEMPO or 4-monosubstituted-TEMPO is employed in polymerization-inhibiting effective amount relative to the vinyl-aryl monomer that is approximately the same as (i.e., within ±50% of, preferably within ±20% of, and more preferably within ±10% of) the polymerization-inhibiting effective amount of the substituted amidine of formula (I) or prototropic tautomer thereof.

In other such embodiments the one or more vinyl-aryl monomer polymerization inhibitors comprises molecular oxygen. More preferably, the invention inhibitor composition further comprises molecular oxygen, wherein the molecular oxygen functions in such a way so as to increase vinyl-aryl polymerization-inhibiting effectiveness of the inhibitor composition compared to vinyl-aryl polymerization-inhibiting effectiveness of the inhibitor composition lacking molecular oxygen. The molecular oxygen can be introduced into the mixture of the inhibitor composition by any effective means. Examples of such introducing means are bubbling air or oxygen gas through the inhibitor composition, adding a liquid (e.g., water) containing molecular oxygen dissolved therein to the inhibitor composition, or a combination thereof. The polymerization-inhibiting effectiveness can be determined by measuring time to gel formation of test mixtures of the invention composition according to a procedure as described in the Examples later. A longer time to gel formation means a greater polymerization-inhibiting effectiveness.

In still more preferred embodiments, the invention also contemplates employing mixtures of two or more such preferred vinyl-aryl monomer polymerization inhibitors other than the substituted amidine of formula (I) or prototropic tautomer thereof. Thus in still more preferred embodiments, the invention inhibitor composition further comprises molecular oxygen and either 4-hydroxy-TEMPO or 4-oxo-TEMPO.

In some embodiments the invention anticipates that 4,6-dinitro-2-(1-methylpropyl)-phenol, copper salts, or both can reduce polymerization-inhibiting effectiveness of the substituted amidine of formula (I). Accordingly, it is preferred in some embodiments that the invention inhibitor composition substantially lacks 4,6-dinitro-2-(1-methylpropyl)-phenol, copper salts, or, more preferably, both.

In some embodiments the invention anticipates that it can be desirable to employ the invention inhibitor composition in a setting where the vinyl-aryl monomer is in contact with water. An example of such a setting is a steam distillation of the vinyl-aryl monomer or an aqueous extraction of the mixture containing the vinyl-aryl monomer, where the aqueous extraction deposits a residual amount of water in contact with the mixture. Accordingly, it is preferred in some embodiments that the inhibitor composition further comprises water.

The invention inhibitor composition can be employed with, and are useful for inhibiting polymerization of, any vinyl-aryl monomer. Certain vinyl-aryl monomers such as styrene and divinylbenzenes are more commonly used in commercial processes than other vinyl-aryl monomers. Accordingly, it is preferred in some embodiments that the vinyl-aryl monomer is styrene, a divinylbenzene, or a mixture of two or more thereof.

As mentioned before, the invention contemplates employing the substituted amidine of formula (I) and the prototropic tautomer thereof. While prototropic tautomerism is well known it might be helpful to illustrate aspects of it here. As shown in formula (I), there are two nitrogen atoms, a right-most one and a left-most one. The right-most nitrogen atom is shown bonded to a hydrogen atom and the left-most one is shown as comprising a nitrogen-carbon double bond. Naturally, each of the left- and right-most nitrogen atoms has a lone pair of electrons (not shown). The prototropic tautomer of the substituted amidine of formula (I) is a substituted amidine of formula (It):

(It)

The prototropic tautomerism is naturally done in such a way that a general syn orientation is maintained in both formula (I) and formula (It). That is, the hydrogen atom bonded to the right-most nitrogen atom in formula (I), or left-most atom in formula (It), and the nitrogen lone pair of electrons (not shown) on the left-most nitrogen atom in formula (I), or right-most atom in formula (It), are oriented in a same general direction, i.e., are generally syn oriented, not anti oriented.

In some embodiments the invention employs the substituted amidine of formula (I) and the prototropic tautomer thereof as shown in formula (It), which formulas interconvert between, and are in equilibrium with, each other in the embodiments. In other embodiments there might be no equilibrium or a rate of conversion from formula (I) form to formula (It) form might be substantially slow compared to a rate of inhibiting polymerization of the vinyl-aryl monomer (e.g., due to different affects of temperature of the invention inhibitor composition on said rates). In such other embodiments the invention contemplates employing the substituted amidine of formula (I), but not the prototropic tautomer thereof, or employing the prototropic tautomer of formula (It), but not the substituted amidine of formula (I).

In some embodiments the invention inhibitor composition is as described later in any one of the Examples thereof.

Figure 1:
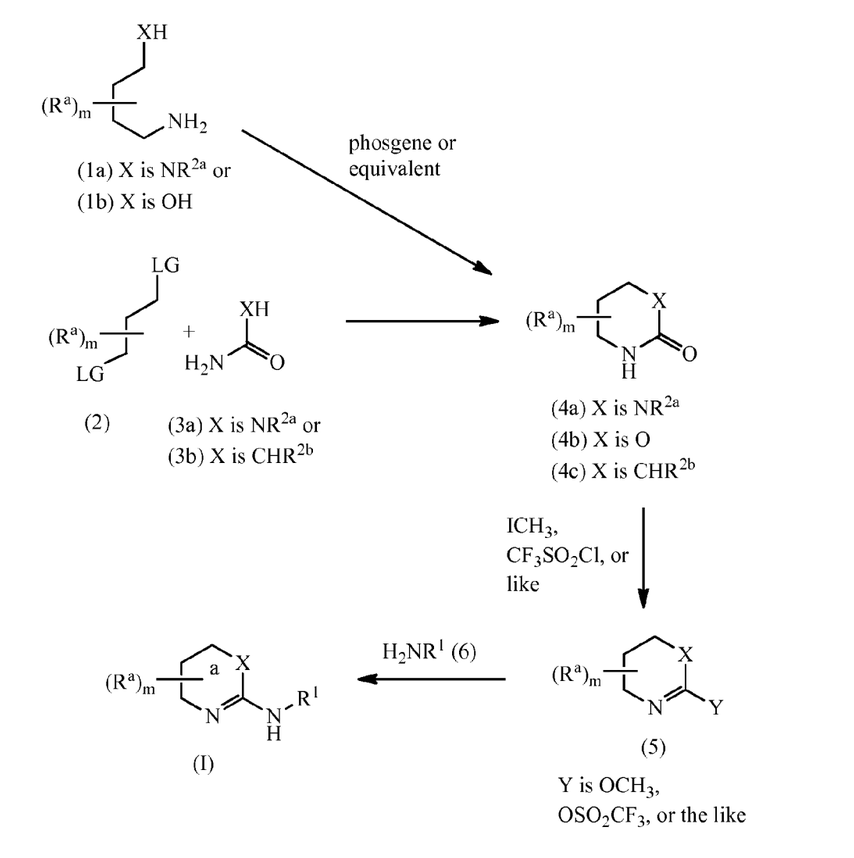
The FIGURE shows a general synthesis of the substituted amidine of formula (II) and the prototropic tautomer thereof.

The substituted amidine of formula (I) can be prepared by any synthetic method, including by conventional means. As mentioned before, the FIGURE shows a general synthesis of the substituted amidine of formula (II) and the prototropic tautomer thereof. In the FIGURE a diamine (1a) or amino alcohol (1b) is reacted with phosgene or an equivalent in presence of a non-nucleophilic base (e.g., triethylamine or sodium hydride) in an aprotic solvent (e.g., toluene, methylene chloride, or acetonitrile) at a temperature of from −78° C. to about 100° C. to give cyclic urea (4a) or cyclic carbamate (4b), respectively. In another approach, a difunctional compound (2), wherein LG is a leaving group such as bromo, iodo, trifluoroacetoxy, or tosyloxy) is condensed with a urea (3a) or carboxamide (3b) in a protic or aprotic, non-nucleophilic solvent (e.g., ethanol, acetone, or acetonitrile), optionally in presence of a non-nucleophilic base, at a temperature of from −20° C. to about 200° C. to give cyclic urea (4a) or lactam (4c). The cyclic urea (4a), cyclic carbamate (4b), or lactam (4c) is then reacted with an activating group such as methyl iodide, trifluoromethanesulfonyl chloride, or the like to prepare compound (5), wherein compound (5) wherein X is as defined for (4a) to (4c), respectively. Compound (5) is then reacted with amine (6) in a protic or aprotic, non-nucleophilic solvent (e.g., ethanol, acetone, or acetonitrile), optionally in presence of a non-nucleophilic base, at a temperature of from −20° C. to about 200° C. to give the substituted amidine of formula (II). In formula (II) when $R^1$ and $R^{2a}$ or are taken together to form a $(C_2-C_4)$alkylene or $(C_1-C_3)$heteroalkylene, then X in diamine (1a) or urea (3a) is HN—$((C_2-C_4)$alkylene or $(C_1-C_3)$heteroalkylene)-NHPG, wherein PG is an amine protecting group as described later. In formula (I) when $R^1$ and $R^{2b}$ or are taken together to form a $(C_2-C_4)$alkylene or $(C_1-C_3)$ heteroalkylene, then X in carboxamide (3b) is CH—$((C_2-C_4)$alkylene or $(C_1-C_3)$heteroalkylene) —NHPG, wherein PG is an amine protecting.

As an alternative to the synthesis illustrated in FIG. 1, the substituted amidine of formula (II) when X is NR $R^{2a}$ or CH $R^{2b}$ can be prepared by partially hydrogenating a corresponding pyrimidine analog or pyridine analog or partially dehydrogenating a corresponding piperidine analog or hexahydropyrimidine analog.

As another alternative to the synthesis illustrated in the FIGURE especially wherein X is $NR^{2a}$; and $R^1$ and $R^{2a}$ are taken together to form $Z^A$, the method of United States Patent Application Publication Number US 2009/0286978 A1 can be employed.

Syntheses of some of the substituted amidine of formula (I) may utilize starting materials, intermediates, or reaction products that contain more than one reactive functional group. During chemical reactions, a reactive functional group may be protected from unwanted side reactions by a protecting group that renders the reactive functional group substantially inert to the reaction conditions employed. A protecting group is selectively introduced onto a starting material or intermediate prior to carrying out the reaction step for which the protecting group is needed. Once the protecting group is no longer needed, the protecting group can be removed. It is well within the ordinary skill in the art to introduce protecting groups during a synthesis and then later remove them. Procedures for introducing and removing protecting groups are known, for example, in Protective Groups in Organic Synthesis, 3rd ed., Greene T. W. and Wuts P. G., Wiley-Interscience, New York, 1999. The following moieties are examples of protecting groups that may be utilized to protect amino, hydroxy), or other reactive functional groups: carboxylic acyl groups such as, for example, formyl, acetyl, and trifluoroacetyl; alkoxycarbonyl groups such as, for example, ethoxycarbonyl, tert-butoxycarbonyl (BOC), β,β,β-trichloroethoxycarbonyl (TCEC), and β-iodoethoxycarbonyl; aralkyloxycarbonyl groups such as, for example, benzyloxycarbonyl (CBZ), para-methoxybenzyloxycarbonyl, and 9-fiuorenylmethyloxycarbonyl (FMOC); trialkylsilyl groups such as, for example, trimethylsilyl (TMS) and tert-butyldimethylsilyl (TBDMS); and other groups such as, for example, triphenylmethyl (trityl), tetrahydropyranyl, vinyloxycarbonyl, ortho-nitrophenylsulfenyl, diphenylphosphinyl, para-toluenesulfonyl (Ts), mesyl, trifluoromethanesulfonyl, methoxymethyl (MOM), and benzyl. Examples of procedures for removing protecting groups include hydrogenolysis of CBZ groups using, for example, hydrogen gas at about 3.4 atmospheres in the presence of a hydrogenation catalyst such as 10% palladium on carbon, acidolysis of BOC or MOM groups using, for example, hydrogen chloride in dichloromethane or trifluoroacetic acid (TFA) in dichloromethane, reaction of silyl groups with fluoride ions, and reductive cleavage of TCEC groups with zinc metal.

As mentioned previously, the invention contemplates the method of inhibiting polymerization of the vinyl-aryl monomer. The invention method employs the substituted amidine of formula (I), invention inhibitor composition, or both.

Environmental conditions are not critical to the invention method. The invention method contemplates employing the substituted amidine of formula (I), the invention inhibitor composition or both in any environmental conditions. For example, the invention method contemplates employing the substituted amidine of formula (I) or the invention inhibitor composition at ambient temperature or lower during transportation or storage of the vinyl-aryl monomer or, preferably, at elevated temperature when purifying the vinyl-aryl monomer (e.g., by distillation) or employing the vinyl-aryl monomer in a reaction process (e.g., a reaction process for synthesizing the vinyl-aryl monomer or for reacting a reactant in presence of the vinyl-aryl monomer). The invention method preferably employs one of the preferred embodiments of the substituted amidine of formula (I) or the invention inhibitor composition as described herein.

In some embodiments the invention method is as described later in any one of the Examples thereof.

As mentioned before, each of the substituted amidine of formula (I) and the invention inhibitor composition independently is useful for inhibiting polymerization of the vinyl-aryl monomer until such a time that polymerization of the vinyl-aryl monomer is desired. At the time when polymerization of the vinyl-aryl monomer is desired, the polymerization of the vinyl-aryl monomer can be performed by any one of a number of ways. One way, for example, comprises exposing the inhibitor composition to vinyl-aryl monomer polymerization inducing conditions, thereby effecting polymerization of the vinyl-aryl monomer in presence of the substituted amidine of formula (I). Another way comprises first separating the vinyl-aryl monomer from the substituted amidine of formula (I) such as by distillation of the vinyl-aryl monomer therefrom. Distillation of the vinyl-aryl monomer preferably gives a distillate comprising distilled vinyl-aryl monomer and substantially lacking the substituted amidine of formula (I). The distillate can then be exposed to the vinyl-aryl monomer polymerization inducing conditions, thereby effecting polymerization of the vinyl-aryl monomer in absence of all or substantially all of the substituted amidine of formula (I).

The invention contemplates employing any polymerization inducing conditions. Preferably, the vinyl-aryl monomer polymerization inducing conditions comprise, for example, elevated temperature (e.g., 100 degrees Celsius (° C.) or higher), contacting with a vinyl-aryl monomer polymerization initiating agent (e.g., benzoyl peroxide or azobisisobutyronitrile) The invention contemplates other methods of effecting such polymerization at a time when such polymerization is desired.

As mentioned previously, the substituted amidine of formula (I), the invention inhibitor composition, or both can be employed in the invention process to build (i.e., increase) molecular weight of a polystyrene. Without being bound by theory, it is believed that the invention process effects a radical polymerization of styrene monomer to the polystyrene.

The polystyrene employed in the invention process is one that is in need of increased molecular weight (e.g., first polystyrene). Typically the polystyrene in need thereof comprises repeat units derived from styrene monomer and is capable of being further reacted with styrene monomer via a controlled radical polymerization so as to add styrene repeat units thereto, thereby building the molecular weight thereof. Without being bound by theory, when the invention process allows styrene monomer to react with or polymerize to the first polystyrene via a nitroxide-mediated polymerization (NMP) variation of controlled radical polymerization (CRP).

Preferably the molecular weight being increased is number average molecular weight ($M_n$). That is, the process produces the second polystyrene wherein the $M_n$ of the second polystyrene is greater than the $M_n$ of the first polystyrene.

In some embodiments the invention process is as described later in any one of the Examples thereof.

In some embodiments the invention is a novel polystyrene produced by the invention process, that is the second polystyrene having increased $M_n$. The second polystyrene having increased $M_n$ is useful in applications that include, but are not limited to, building insulation, synthetic rubber, thermoplastics, fiberglass, piping, automobile and boat parts, food containers, carpet backing, and ion exchange resins. Likewise, polymers prepared from one or more of the vinyl-aryl monomers are also useful in the foregoing applications.

The invention also contemplates an article of chemical equipment comprising an inhibitor-functionalized coating comprising a derivative of the substituted amidine of formula (I) that is covalently bonded to an organic polymer coating of a coated internal element of the article of chemical equipment (e.g., reactor, distillation column, pipe, chemical storage tank, and the like). The covalent bond would be from an atom (e.g., C or N or O, if any) of the organic polymer and to a carbon atom, or nitrogen atom or oxygen atom, if any, of the substituted amidine of formula (I) other than the two nitrogen atoms shown in formula (I). The inhibitor-functionalized coating would contain a polymerization-inhibiting effective amount of the derivative such that the derivative would be capable of inhibiting polymerization of vinyl-aryl monomers in contact with the inhibitor-functionalized coating (e.g., vinyl-aryl monomer being distilled through a coated distillation column).

Illustrative examples of the present invention are provided later where the examples employ certain methods and materials, which include certain preparations. The methods and materials and preparations are described in the following section.

Methods, Materials and Preparations

Divinylbenzenes Mixture A used in the Preparations and Examples is a mixture of an approximately 2:1 molar ratio of 1,3-divinylbenzene to 1,4-divinylbenene.

N,N'-Dicyclohexyl-morpholine-4-carboxamidine has CAS Registry Number 4975-73-9 (Compound (g5)).

1,5,7-Triazabicyclo[4.4.0]dec-5-ene has CAS Registry Number 5807-14-7 (Compound (g1)); pKa 26.0. Commercially available from the Aldrich Chemical Company, St. Louis, Mo., USA.

Determine monomer conversions from the concentration of the unreacted monomer in the samples periodically remove from the reactions using a Shimadzu GC-14A gas chromatograph, equipped with a capillary column (DBWax, 30 m×0.54 mm×0.5 µm, J&W Scientific). Use toluene as internal standard for calculation of monomer conversions.

Characterize the polymer samples by gel permeation chromatography (GPC) (Polymer Standards Services (PSS) columns (guard, $10^5$, $10^3$, and $10^2$ Å), with tetrahydrofuran (THF) eluent at 35° C., flow rate=1.00 mL/minute, and differential refractive index (RI) detector (Waters, 2410)). Use diphenyl ether as the internal standard to correct the fluctuation of the THF flow rate. Determine apparent molecular weights and polydispersity with a calibration based on linear polystyrene standards using WinGPC 6.0 software from PSS.

For some of the experiments, monitor conversion by taking timed samples, dissolving in $CDCl_3$, and analyzing by $^1H$ NMR as a comparison of integration of vinyl peaks ($\delta$5.8-5.2) to alkyl peaks of toluene and ethylbenzene ($\delta$ 2.6-2.7). Also visually observe test compositions for signs of gelation, and record time when gelation is first observed. The longer a period from a Time 0 to time of gelation, the better the test substance or compound is as an inhibitor or polymerization of the vinyl-aryl monomer(s).

Non-limiting examples of the present invention are described below that illustrate some specific embodiments and aforementioned advantages of the present invention. Preferred embodiments of the present invention incorporate one limitation, and more preferably any two, limitations of the Examples, which limitations thereby serve as a basis for amending claims.

EXAMPLE(S) OF THE PRESENT INVENTION

Examples 1 to 8

Compositions Comprising Mixtures of Substituted Amidine and Divinylbenzenes Mixture a and their use to inhibit polymerization of divinylbenzenes In separate test tubes mix Divinylbenzenes Mixture A, a polymerization inhibiting effective amount, expressed in parts per million (ppm) by mass, of the substituted amidine of formula (I), and any optional ingredient(s) together to form compositions of Examples 1 to 8 as described below in Table 1. Degas test tubes by 20 minutes of nitrogen gas bubbling. Then place the tubes in an oil bath thermostated at 115° C., and note the time at which a gel has formed for each tube. For some of the experiments, monitor conversion by taking timed samples, dissolving in CDCl$_3$, and analyzing by $^1$H NMR as a comparison of integration of vinyl peaks (δ 5.8-5.2) to alkyl peaks of toluene and ethylbenzene (δ 2.6-2.7). Results are reported in Table 1.

For comparison, results for a non-invention baseline neat Divinylbenzenes Mixture A (i.e., lacking any polymerization inhibitor) heated at 115° C. for 24 hours ("Baseline") are also shown in Table 1.

Examples 10 to 13

Compositions Comprising Mixtures of Substituted Amidine and Divinylbenzenes and their use to Inhibit Polymerization of Styrene Allow four weighed 20-mL size vials containing known amounts of compound (g1) (about 100 milligrams (mg) measured in a drybox) to stand exposed to air for 30 minutes, 1 hour, 2 hours, and 3 hours, respectively, so as to absorb increasing amounts of water from the air to give samples of water-containing compound (g1). Reweigh vials to determine increase in mass due to absorption of water. The four samples of water-containing compound (g1) respectively contain 12.2 mole percent water (mol %; (average of 4 values), 15 mol % water (average of 3 values), 18.3 mol % water (average of 2

TABLE 1 compositions of substituted amidine and Divinylbenzenes Mixture A and their use to inhibit polymerization of divinylbenzenes

| Example Number | Substituted amidine Compound Number | Atmosphere | Amount of (g1) (ppm) | Additional ingredient(s) (Amounts in ppm) | Time to gelation |
|---|---|---|---|---|---|
| Baseline N/a* | None | air | N/a | None | 0.25 hour to <0.75 hour |
| 1 | (g1) | air | 5000 | None | 7.5 hours (average of at least two runs) |
| 2 | (g1) | air | 500 | 4-BuO-TEMPO (5000) | 9.6 hours |
| 3 | (g1) | air | 5000 | 4-BuO-TEMPO (5000) | 28 hours |
| 4 | (g1) | air | 5000 | 4-BuO-TEMPO (5000) | 27 hours |
| 5 | (g1) | air | 5000 | 4-BuO-TEMPO (500) | 13 hours |
| 6 | (g1) | air | 500 | DNBP** (5000) | 8.5 hours |
| 7 | (g1) | air | 5000 | DNBP (5000) | 2 hours |
| 8 | (g1) | Oxygen-free | 5000 | None | 30 minutes |

*N/a means not applicable;
**DNBP means 2-(secondary-butyl)-4,6-dinitrophenol.

The compositions of Examples 1 to 7 are useful, and the compositions of Examples 1 to 5 are particularly useful, for inhibiting polymerization of divinylbenzenes.

Example 9

Composition Comprising a Mixture of Substituted Amidine Compound (g1) and Styrene and its use to Inhibit Polymerization of Styrene In a test tube mix styrene and a polymerization inhibiting effective amount, expressed in parts per million (ppm) by mass, of compound (g1) together to form invention composition of Example 9. In an air atmosphere, stopper the test tube with rubber septa and heat the composition at 115° C. for 24 hours while monitoring same by $^1$H-NMR. After 24 hours no polystyrene is observed in $^1$H-NMR. A 15% loss of styrene is observed by $^1$H-NMR, believed to be due to Diels-Alder adduct formation therefrom.

For comparison, heating neat styrene at 115° C. produces a 37% loss of styrene after 4 hours, where the loss of styrene is by way of polymerization thereof to polystyrene.

values), and 20.6 mol % (1 value) water. In separate test tubes mix under air atmosphere Divinylbenzenes Mixture A, a polymerization inhibiting effective amount, expressed in parts per million (ppm) by mass, of different ones of the water-containing compound (g1) together to form invention compositions of Examples 10 to 13. Then place the tubes in an oil bath thermostated at 115° C., and note the time at which a gel has formed for each tube. Results are reported in Table 2 along with time to gelation for a non-invention baseline comparison ("Baseline") with neat styrene (i.e., lacking any polymerization inhibitor).

TABLE 2 compositions of substituted amidine and divinylbenzenes and their use to inhibit polymerization of divinylbenzenes

| Example Number | Substituted amidine Compound Number and mol % water content | Amount of (g1) (ppm) | Additional ingredient(s) (Amounts in ppm) | Time to gelation |
|---|---|---|---|---|
| 10 | (g1) with 12.2 mol % H$_2$O | 5000 | None | 7.7 hours |

TABLE 2-continued compositions of substituted amidine and divinylbenzenes and their use to inhibit polymerization of divinylbenzenes

| Example Number | Substituted amidine Compound Number and mol % water content | Amount of (g1) (ppm) | Additional ingredient(s) (Amounts in ppm) | Time to gelation |
|---|---|---|---|---|
| 11 | (g1) with 15 mol % $H_2O$ | 5000 | None | 7.5 hours |
| 12 | (g1) with 18.3 mol % $H_2O$ | 5000 | None | 8 hours |
| 13 | (g1) with 20.6 mol % $H_2O$ | 5000 | None | 6.5 hours |

*N/a means not applicable.

Examples 14 to 17

Compositions Comprising Mixtures of Substituted Amidine and Styrene and their use to Increase Molecular Weight of Polystyrene In separate experiments, add styrene (10 mL, 87.3 mmol) to a 10-mL size Schlenk flask together with benzoyl peroxide (BPO) (1.1 mg, 0.0044 mmol) and 2,2,6,6-tetramethylpiperidine-1-oxyl (TEMPO) (1.4 mg, 0.0088 mmol) as a stock solution in 1 mL toluene. Add a certain amount of compound (g1) (see Table 3 below for concentrations), with the concentration being in ppm by mass versus styrene. Molar ratio of styrene:TEMPO:BPO:(g1) is 10,000:1:0.5:(0.5, 5, 50, or 10), respectively, to give the composition of Example 14, 15, 16, or 17.

Seal the flask and bubble with nitrogen gas for 30 minutes. After which time, place the flask in an oil bath thermostated at 135° C. Periodically take timed samples and analyze them using gas chromatography and GPC., to form compositions of Examples 14 to 17 as described below in Table 3. Purge the flasks with nitrogen gas, and heat the compositions at 135° C. for 18 to 50 hours while monitoring polystyrene production. Results are reported in Table 3.

TABLE 3 compositions of substituted amidine and styrene and their use to increase molecular weight of polystyrene

| Example Number | Substituted amidine Compound Number and mol % water content | Amount of (g1) (ppm) | Additional ingredient(s) (Amounts in ppm) | Number average molecular weight ($M_n$) of polystyrene (g/mol) |
|---|---|---|---|---|
| 14 | (g1) | 50 | TEMPO, BPO | 72,500 at 1.5 hours; 117,000 at 3.3 hours; 131,000 at 8.7 hours |
| 15 | (g1) | 500 | TEMPO, BPO | 104,000 at 18 hours; 114,000 at 22 hours; 180,000 at 46 hours |
| 16 | (g1) | 5000 | TEMPO, BPO | 123,000 at 28 hours |
| 17 | (g1) | 1000 | TEMPO, BPO | 264,000 at 18 hours** |

*N/a means not applicable;
**weight average molecular weight ($M_w$) for Ex. 17 is 502,000 g/mol.

Examples 18s to 22s and 18v to 22v

Compositions Comprising Mixtures of Styrene or Divinylbenzene and 4000 Ppm of any one of Compounds (g2) to (g6), Respectively In separate 50-mL sized flasks, 10.0 g of styrene and a styrene polymerization inhibiting amount of 0.040 g of one of the aforementioned compounds (g2) to (g6), respectively, can be mixed together to produce the compositions of Examples 18s to 22s, respectively.

In separate 50-mL sized flasks, 10.0 g of Divinylbenzenes Mixture A and a divinylbenzene polymerization inhibiting amount of 0.040 g of one of the aforementioned compounds (g2) to (g6), respectively, can be mixed together to produce the compositions of Examples 18v to 22v, respectively.

Examples 23s, 24s, 23v, and 24v

Compositions Comprising Mixtures of Styrene or Divinylbenzene and 6000 ppm of any one of Compounds (i1) and (i2), Respectively In separate 50-mL sized flasks, 10.0 g of styrene and a styrene polymerization inhibiting amount of 0.060 g of one of the aforementioned compounds (i1) and (i2), respectively, can be mixed together to produce the compositions of Examples 23s and 24s, respectively.

In separate 50-mL sized flasks, 10.0 g of Divinylbenzenes Mixture A and a divinylbenzene polymerization inhibiting amount of 0.060 g of one of the aforementioned compounds (i1) and (i2), respectively, can be mixed together to produce the of Examples 23v and 24v, respectively.

Examples 25s to 29s and 25v to 29v

Compositions Comprising Mixtures of Styrene or Divinylbenzene and 5000 ppm of any one of Compounds (c1) to (c5), Respectively In separate 50-mL sized flasks, 10.0 g of styrene and a styrene polymerization inhibiting amount of 0.050 g of one of the aforementioned compounds (c1) to (c5), respectively, can be mixed together to produce the compositions of Examples 25s to 29s, respectively.

In separate 50-mL sized flasks, 10.0 g of Divinylbenzenes Mixture A and a divinylbenzene polymerization inhibiting amount of 0.050 g of one of the aforementioned compounds (c1) to (c5), respectively, can be mixed together to produce the compositions of Examples 25v to 29v, respectively.

Example 30

Composition Comprising a Mixture of Molecular Oxygen, Substituted Amidine Compound (g1), and Styrene and its use to Inhibit Polymerization of Styrene In a test tube mix styrene and a 5000 ppm polymerization inhibiting effective amount of compound (g1) together to form invention composition of Example 30. Molecular oxygen can be bubbled through the mixture in such a way that a composition having an increased vinyl-aryl polymerization-inhibiting effectiveness compared to vinyl-aryl polymerization-inhibiting effectiveness of the invention composition of Example 8, thereby producing the composition of Example 30. In an air atmosphere, stopper the test tube with a rubber septum, and heat the composition of Example 30 at 115° C. for 24 hours, while monitoring same by $^1$H-NMR, so as to inhibit polymerization of styrene therewith. Gel formation can occur after 6 hours for Example 30 versus at 30 minutes for Example 8.

Examples 31a and 31b

Compositions Comprising (a) A Mixture of Molecular Oxygen, Substituted Amidine Compound (g1), and Styrene or (b) A Mixture of Molecular Oxygen, 4-oxo-TEMPO, Substituted Amidine Compound (g1), and Styrene, and their use to Inhibit Polymerization of Styrene In separate test tubes, mix under air atmosphere styrene and either (a) a 100 ppm polymerization inhibiting effective amount of compound (g1) or (b) 50 ppm polymerization inhibiting effective amount of compound (g1) and 50 ppm polymerization inhibiting effective amount of 4-oxo-TEMPO together to form invention composition of Example 31a or 31b, respectively. In an air atmosphere, stopper the test tubes with rubber septa, and heat the compositions of Examples 31a and 31b at 115° C. for 1440 minutes, while monitoring same by $^1$H-NMR, so as to inhibit polymerization of styrene therewith. Results are reported later in Table 4.

For baseline comparison purposes, repeat the procedure of Example 31b two times except a first time omit both compound (g1) and 4-oxo-TEMPO and a second time omit compound (g1) and employ 100 ppm of 4-oxo-TEMPO. Results are reported below in Table 4.

TABLE 4 compositions of substituted amidine and styrene and their use to inhibit polymerization of styrene with and without 4-oxo-TEMPO compared to baseline compositions.

| Example Number | Substituted amidine Compound Number | Atmosphere | Amount of (g1) (ppm) | Additional ingredient(s) (Amounts in ppm) | Time (min) | Conversion by $^1$H NMR (%) |
|---|---|---|---|---|---|---|
| Baseline | None | air | N/a | None | 80 | 5.6 |
| | | | | | 160 | 10.2 |
| | | | | | 240 | 13.0 |
| | | | | | 360 | 25.7 |
| | | | | | 1440 | N/a |
| Baseline | None | air | N/a | 4-oxo-TEMPO, (100) | 80 | N/d |
| | | | | | 160 | N/d |
| | | | | | 240 | N/d |
| | | | | | 360 | 8.15 |
| | | | | | 1440 | N/a |
| 31a | (g1) | air | 100 | None | 80 | N/d |
| | | | | | 160 | 2.9 |
| | | | | | 240 | 8.7 |
| | | | | | 360 | 18.4 |
| | | | | | 1440 | N/a |
| 31b | (g1) | air | 50 | 4-oxo-TEMPO, (50) | 80 | N/d |
| | | | | | 160 | N/d |
| | | | | | 240 | N/d |
| | | | | | 360 | traces |
| | | | | | 1440 | 22.7 |

N/a means not applicable; and N/d means not detected.

As shown by the Examples, the substituted amidine of formula (I), the invention inhibitor composition, or both independently are useful for inhibiting polymerization of the vinyl-aryl monomer therein until such a time that polymerization of the vinyl-aryl monomer is desired. The substituted amidine of formula (I), invention inhibitor composition, or both is also useful for building molecular weight of a polystyrene as described herein.

While the present invention has been described above according to its preferred aspects or embodiments, it can be modified within the spirit and scope of this disclosure. This application is therefore intended to cover any variations, uses, or adaptations of the present invention using the general principles disclosed herein. Further, the application is intended to cover such departures from the present disclosure as come within the known or customary practice in the art to which this present invention pertains and which fall within the limits of the following claims.

What is claimed is:

1. An inhibitor composition comprising a mixture of a vinyl-aryl monomer and a polymerization-inhibiting effective amount of a substituted amidine of formula (I):

(I)

or a prototropic tautomer thereof,

Wherein: Z is 1,3-($C_3$ or $C_7$)hydrocarbylene or 1,3-($C_2$-$C_6$) heterohydrocarbylene such that ring (r) is a six-membered ring; benzo-fused substituted six-membered ring wherein Z comprises a 3-atom linker portion having 2 contiguous ring carbon atoms that are fused to the benzo; or 5-membered or 6-membered heteroarylene-fused substituted six-membered ring wherein Z comprises a 3-atom linker portion having 2 contiguous ring carbon atoms that are fused to the 5-membered or 6-membered heteroarylene, wherein when Z is unsubstituted, ring (r) is non-aromatic and when Z is substituted, ring (r) is non-aromatic or aromatic; and (a), (b), or (c):

(a) X is $NR^{2a}$, $C(H)R^{2b}$, or O; and

Each of $R^1$, $R^{2a}$, and $R^{2b}$ independently is a hydrogen atom, ($C_1$-$C_{20}$)hydrocarbyl, or ($C_1$-$C_{20}$)heterohydrocarbyl;

(b) X is NR$^{2a}$; and
R$^1$ and R$^{2a}$ are taken together to form Z$^A$, wherein Z$^A$ independently is as defined for Z; or
(c) X is C(H)R$^{2b}$; and
R$^1$ and R$^{2b}$ independently are taken together to form Z$^A$, wherein Z$^A$ independently is as defined for Z;
Wherein each heterohydrocarbylene, and heterohydrocarbyl independently comprises carbon atoms, hydrogen atoms, and 1 or 2 heteroatoms wherein each heteroatom independently is O, S, S(O), S(O)$_2$, or N(R$^N$);
Wherein each R$^N$ independently is a hydrogen atom or unsubstituted (C$_1$-C$_{10}$)alkyl;
Wherein each benzo, heteroarylene, hydrocarbylene, heterohydrocarbylene, hydrocarbyl, and heterohydrocarbyl independently is unsubstituted or substituted with from 1 to 3 substituents R$^S$; and
Wherein each R$^S$ independently is bonded to a carbon atom and is unsubstituted (C$_1$-C$_{10}$)alkyl, unsubstituted (C$_3$-C$_{10}$)cycloalkyl, unsubstituted (C$_1$-C$_{10}$)alkyl-O—, —OH, oxo (i.e., =O), or fluorine atom.

2. The inhibitor composition as in claim 1, represented by formula (II):

(II)

or a prototropic tautomer thereof,
Wherein m is an integer of from 0 to 3 and R$^1$ and R$^{2a}$ are as defined in (a) or (b) of claim 1.

3. The inhibitor composition as in claim 2, represented by formula (IIa):

(IIa)

or a prototropic tautomer thereof,
wherein n is an integer of from 0 to 3.

4. The inhibitor composition as in claim 3, wherein m and n are each 0 such that the compound of formula (IIa) is compound (g1):

(g1)

or the prototropic tautomer thereof.

5. The inhibitor composition as in claim 3, wherein m and n are each 2 such that the compound of formula (IIa) is compound (g2), (g3), or (g7):

(g2)

(g3)

(g7)

or the prototropic tautomer thereof.

6. The inhibitor composition as in claim 2, wherein the compound of formula (II) is any one of compounds (g4) to (g6):

(g4)

(g5)

(g6)

or the prototropic tautomer thereof.

7. The inhibitor composition as in claim 1, wherein X is O such that the substituted amidine of formula (I) is a compound of formula (III):

(III)

or a prototropic tautomer thereof,
Wherein m is an integer of from 0 to 3.

8. The inhibitor composition as in claim 7, wherein the compound of formula (III) is compound (i1) or (i2):

(i1)

(i2)

or the prototropic tautomer thereof.

9. The inhibitor composition as in claim 1, wherein X is C(H)R$^{2b}$ such that the substituted amidine of formula (I) is a compound of formula (IV):

(IV)

or a prototropic tautomer thereof, wherein m is an integer of from 0 to 3 and $R^1$ and $R^{2b}$ are as defined in (a) or (c) of claim 1.

10. The inhibitor composition as in claim 9, wherein the compound of formula (IV) is any one of compounds (c1) to (c3):

or the prototropic tautomer thereof.

11. The inhibitor composition as in claim 9, wherein the compound of formula (IV) is compound (c4) or (c5):

or the prototropic tautomer thereof.

12. The inhibitor composition as in claim 1, wherein the NH in the substituted amidine of formula (I) is characterizable by a pKa of from 25 to 27.

13. The inhibitor composition as in claim 1, wherein the mixture of the inhibitor composition further comprises one or more vinyl-aryl monomer polymerization inhibitors other than the substituted amidine of formula (I) or prototropic tautomer thereof.

14. The inhibitor composition as in claim 13, wherein the one or more vinyl-aryl monomer polymerization inhibitors other than the substituted amidine of formula (I) or prototropic tautomer thereof comprises molecular oxygen, 2,2,6,6-tetramethylpiperidine-1-oxyl, or a 4-monosubstituted 2,2,6,6-tetramethylpiperidine-1-oxyl.

15. The inhibitor composition as in claim 14, wherein the one or more vinyl-aryl monomer polymerization inhibitors other than the substituted amidine of formula (I) or prototropic tautomer thereof comprises molecular oxygen and either 4-hydroxy-2,2,6,6-tetramethylpiperidine-1-oxyl or 4-oxo-2,2,6,6-tetramethylpiperidine-1-oxyl.

16. The inhibitor composition as in claim 14, wherein the molecular oxygen functions in such a way so as to increase vinyl-aryl polymerization-inhibiting effectiveness of the inhibitor composition compared to vinyl-aryl polymerization-inhibiting effectiveness of the inhibitor composition lacking molecular oxygen.

17. The inhibitor composition as in claim 1, or the prototropic tautomer thereof, wherein the inhibitor composition lacks 4,6-dinitro-2-(1-methylpropyl)-phenol, copper, or both.

18. The inhibitor composition as in claim 1, or the prototropic tautomer thereof, wherein the vinyl-aryl monomer is styrene, a divinylbenzene, or a mixture thereof.

19. A method of inhibiting polymerization of a vinyl-aryl monomer, the method comprising contacting a vinyl-aryl monomer in need of polymerization inhibition treatment with a polymerization-inhibiting effective amount of the inhibitor composition as described in claim 1, or the prototropic tautomer thereof, wherein the contacting is performed in such a way that polymerization of the vinyl-aryl monomer is inhibited.

20. A process for building molecular weight of a polystyrene, the process comprising contacting a first polystyrene with a nitroxide radical source and a polymerization-inhibiting effective amount of the inhibitor composition as described in claim 1, or the prototropic tautomer thereof with a vinyl-aryl monomer in such a way that the vinyl-aryl monomer reacts with the first polystyrene so as to form a second polystyrene such that number average molecular weight of the second polystyrene is greater than number average molecular weight of the first polystyrene.

* * * * *